US006641822B2

(12) United States Patent
Eichhorn et al.

(10) Patent No.: US 6,641,822 B2
(45) Date of Patent: *Nov. 4, 2003

(54) COMPOSITION CONTAINING HUMIDITY REGULATORS FOR PREPARING TISSUE PRODUCTS

(75) Inventors: Stephan Eichhorn, Gernsheim (DE); Walter Hill, Lampertheim (DE); Peter von Paleske, Seeheim (DE); Hans Nueunhoeffer, Muhltal (DE)

(73) Assignee: SCA Hygiene Products GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/928,486

(22) Filed: Aug. 14, 2001

(65) Prior Publication Data
US 2002/0028230 A1 Mar. 7, 2002

Related U.S. Application Data

(62) Division of application No. 09/380,283, filed as application No. PCT/EP98/00767 on Feb. 10, 1998, now Pat. No. 6,306,408.

(30) Foreign Application Priority Data

Mar. 19, 1997 (DE) .......................... 197 11 452

(51) Int. Cl.$^7$ .............................. A61K 6/00; A61K 9/00; A61K 9/14
(52) U.S. Cl. ..................... 424/401; 424/400; 424/402; 424/488
(58) Field of Search .............. 435/1.1, 41, 179, 435/325; 424/93.1, 93.7, 400, 401, 402, 488

(56) References Cited

U.S. PATENT DOCUMENTS

| 2,826,551 | A | | 3/1958 | Geen et al. |
| 4,364,837 | A | | 12/1982 | Pader |
| 4,395,454 | A | | 7/1983 | Baldwin |
| 4,664,908 | A | | 5/1987 | Woods et al. |
| 4,882,221 | A | | 11/1989 | Bogart et al. |
| 4,913,828 | A | * | 4/1990 | Caswell et al. ............ 252/88 |
| 4,921,895 | A | | 5/1990 | Schaefer et al. |
| 4,950,545 | A | | 8/1990 | Walter et al. |
| 5,139,781 | A | | 8/1992 | Birtwistle et al. |
| 5,312,522 | A | | 5/1994 | Van Phan et al. |
| 5,397,435 | A | | 3/1995 | Ostendorf et al. |
| 5,405,501 | A | | 4/1995 | Phan et al. |
| 5,409,640 | A | | 4/1995 | Giret et al. |
| 5,427,696 | A | | 6/1995 | Phan et al. |
| 5,716,703 | A | * | 2/1998 | Payne ...................... 428/378 |
| 5,942,238 | A | | 8/1999 | McAtee et al. |
| 5,972,361 | A | | 10/1999 | Fowler et al. |
| 6,008,246 | A | | 12/1999 | Ito et al. |

| 6,306,408 | B1 | * | 10/2001 | Eichhorn et al. ............ 424/401 |

FOREIGN PATENT DOCUMENTS

| AT | 358741 | 1/1978 |
| CA | 2200049 | 9/1995 |
| DE | 2622571 A1 | 12/1977 |
| DE | 2622571 B2 | 3/1978 |
| DE | 3237574 A1 | 4/1984 |
| DE | 8512083 U1 | 4/1985 |
| DE | 3447499 C3 | 7/1986 |
| DE | 4000920 A1 | 7/1991 |
| DE | 4334367 A1 | 4/1995 |
| EP | 0 157 949 A2 | 10/1985 |
| EP | 0 186 208 A2 | 7/1986 |
| EP | 0 282 289 A1 | 9/1988 |
| EP | 0 347 153 A2 | 12/1989 |
| EP | 0 347 154 A2 | 12/1989 |
| EP | 0 347 176 A2 | 12/1989 |
| EP | 0 347 177 B1 | 12/1989 |
| EP | 0 347 177 A2 | 12/1989 |
| EP | 0 688 901 A2 | 12/1995 |
| EP | 0 690 079 A1 | 1/1996 |
| EP | 0 688 901 A3 | 7/1996 |
| GB | 849433 | 9/1960 |
| WO | WO 94/16143 | 7/1994 |
| WO | WO 94/19381 | 9/1994 |
| WO | WO 94/29520 | 12/1994 |
| WO | WO 94/29521 | 12/1994 |
| WO | WO 95/01478 | 1/1995 |
| WO | WO 95/01479 | 1/1995 |
| WO | WO 95/11343 | 4/1995 |
| WO | WO 95/11344 | 4/1995 |
| WO | WO 96/08601 | 3/1996 |

OTHER PUBLICATIONS

Römpp–Chemie–Lexikon, 9$^{th}$ Edition, 1992, pp. 3886–3889.
Renner et al., Resorcin, Band 20, pp. 190–285.
Nowak, G.A.: Amphotenside von Betain–Struktur in der Kosmetik. In: Seifen–Öle–Fette–Wachse, Nr. 15, Jul. 17, 1968.
R. Wachter et al., Parfümerie und Kosmetik (Perfumery and Cosmetics) 75 (1994) p. 755–58, 761.
Ullmann, Enzyklopädie der technischen Chemie (Encyclopedia of Industrial Chemistry), vol. 20, pp. 190–285.

* cited by examiner

Primary Examiner—David M. Naff
Assistant Examiner—Deborah K. Ware
(74) Attorney, Agent, or Firm—Burns, Doane, Swecker & Mathis, L.L.P.

(57) ABSTRACT

A composition is provided containing moisture regulators for tissue products. The composition contains 1% to 15% by weight, preferably 2% to 20% by weight, relative to the total composition, of at least one special non-ionic surfactant selected from among at least one amine oxide and/or hydroxy acid esters and/or at least one ampho-surfactant. Also provided is a tissue product as well as to a process for the production of tissue products.

23 Claims, No Drawings

COMPOSITION CONTAINING HUMIDITY REGULATORS FOR PREPARING TISSUE PRODUCTS

CROSS-REFERENCE TO RELATED APPLICATIONS

This application is a divisional of U.S. application Ser. No. 09/380,283, filed on Aug. 27, 1999, now U.S. Pat. No. 6,306,408, which was a national stage filing under 35 U.S.C. §371 of International Application No. PCT/EP98/00767 filed on Feb. 10, 1998, which International Application was published by the International Bureau on Sep. 24, 1998.

BACKGROUND OF THE INVENTION

1. Field of the Invention

The present invention relates to a composition containing moisture regulators for tissue products, a process for the production of these products, the use of the composition for the treatment of tissue products as well as tissue products in the form of wet-laid, including TAD, or air-laid products (non-wovens) on the basis of sheet-like support materials containing primarily cellulose fibers.

2. Description of the Related Art

The present invention relates to a skin-care as well as softness-enhancing composition for the treatment of tissue products which can be used, for example, for tissue paper such as facial tissues, cosmetic tissues, toilet paper, household paper towels and the like.

Paper cloth, sheets or non-wovens, also called tissue or tissue paper or tissue cloth in the hygienic paper area when they have low basis weights, are articles of daily use which have become indispensable in modem society. Tissue products such as facial tissues, cosmetic tissues, make-up removal wipes, household paper towels and toilet paper make up a large part of the trade volume, whereby there is a tendency towards emollient products. In the case of tissue products with a special emollient character, aside from the skin-care aspect, the aspect of extreme softness of the tissues is also the focus of consumer interest. As far as the skin-care properties are concerned, in addition to the greater softness of the products and the passive skin-care already associated with this, this entails mainly chemical substances that can be applied onto the tissue as a component of a composition. The term "active skin-care" is used below to mean that a composition is applied onto the tissue and then transferred to the skin when this tissue is used. Thus, on the one hand, through the use of a soft tissue, the skin should not be additionally irritated and, on the other hand, if the application quantity is sufficient, the skin should soothed and reddening of the skin largely prevented or at least mitigated. Skin-care components of the composition are those substances that have the effects on the skin of soothing, of preventing or inhibiting irritation, of moisturizing and the like, and that are of the kind known from skin cosmetics as components of skin lotions, skin creams, skin ointments, shampoos, etc.

The term "passive skin-care" is used to describe the gentleness of a tissue product, resulting from extreme softness, that is to say, high surface smoothness/gentleness in conjunction with high crumple softness. This softness can be further improved by the composition and by the morphological structure of the tissue product, by mechanical measures such as smoothing or roughening as well as by the addition of suitable chemical auxiliaries.

In general, "softness" in tissue products refers to the subjective tactile experience of consumers when they take the product into their hands and rub it over their skin or crumple it in their hands. Please refer to the older patent application WO96/08601 for further details on the softness and on the production of the tissue products.

The use of chemicals to increase the softness of tissue products is likewise known.

These chemicals are usually cationic surfactants of the type described in German Preliminary Published Application No. 4,334,367 or EP-A 0,688,901 or else a glucose glutamate of the type found in U.S. Pat. No. 4,882,221. Another possibility for obtaining soft tissue paper is to use non-ionic surfactants of the type described in European Patent Application No. 347,177 or the use of polysiloxanes that are described in greater depth, for example, in European Patent Application Nos. 347,153 and 347,154.

Moreover, a non-drying cleansing cloth is known from DE-C 3,447,499 whereby an emulsion is applied onto a support material, said emulsion consisting of at least one moisture regulator, preferably polyethylene glycol, and at least one additional liquid substance.

Moreover, WO96108601 already described compositions containing polysiloxanes for tissue paper products that contain 25% to 95% by weight of at least one polyhydroxy compound, 5% to 75% by weight of polysiloxane as well as, relative to 100 parts by weight of this mixture, 0% to 35% by weight of water. In this application, it was possible to demonstrate that the above-mentioned combination has a synergistic effect on the softness. The above-mentioned state of the art had always had the objective of creating tissue products with greater softness in which the mechanical properties are not negatively influenced, U.S. Pat. No. 4,786,367 relates to a web of cellulosic fibers containing 0.1% to 2% by weight, relative to the fiber web, of a lauroamphoglycinate. However, this publication contains no information indicating that this fiber web additionally contains moisture regulators, nor does it suggest this.

German Preliminary Published Application No. 3,237,574 relates to the use of special amine oxides of the type defined by the general formula (I) below as an auxiliary in the production of cellulose, paper or special hygiene products in order to reduce the mechanical strength and to Improve the wettability or water absorption capacity. These amine oxides are normally added in quantities of 0.02% to 2.0%, preferably 0.01 to 1%, relative to the dry weight of the cellulose. Here, too, this publication neither describes as prior art nor suggests adding moisture regulators to such compositions for tissue products or to the tissue products themselves.

EP-A 0,347,176 relates to a tissue paper with a basis weight of 10 to 65 grams per $m^2$ and a density of no more than 0.6 grams per $cm^3$, whereby, in addition to cellulose fibers, this paper contains at least 0.01% by weight of a non-cationic surfactant, relative to the dry fiber weight of the paper, whereby said non-cationic surfactant has been applied onto the moist tissue web. The above-mentioned non-cationic surfactant is, for example, a water-soluble amine oxide with an alkyl group having 10 to 15 carbon atoms and 2 (hydroxy)alkyl groups having 1 to 3 carbon atoms. Once again, it cannot be gleaned from this publication to also add moisture regulators to such a composition containing such surfactants and to use this mixture on tissue products, nor is this suggested.

EP-A 0,347,177 defines the product mentioned in EP-A 0,347,176 as well as the applicable production process. Hence, once again, the currently claimed subject matter is neither suggested nor described as prior art.

EP-A 0,688,901 relates to a tissue paper product to which 3% to 35% by dry weight of an aqueous composition that imparts softness has been added, whereby said composition that imparts softness consists of 20% to 98% by weight of glycerin and 0.2% to 5% by weight of a quaternary ammonium compound, which is usually meant to refer to a cationic surfactant rather than a non-ionic or ampho-ionic surfactant. Hence, this publication neither describes as prior art nor suggests the use of specific amounts of a special non-ionic surfactant. A substitution of the cationic surfactant for a non-ionic surfactant is not suggested either, since both substance classes are normally not comparable to each other due to their different realms of application.

DE-C 3,447,499 relates to a non-drying cleansing cloth consisting of a sheet-like support material onto which an emulsion has been applied that contains water and a moisture regulator, whereby fine-particle, inorganic and/or organic dispersible solids have necessarily been applied onto the support material. Once again, it cannot be gleaned from this publication to add even special amounts of a special non-ionic surfactant to such a composition for tissue products or to tissue products themselves, without the corresponding fine-particle, inorganic and/or organic, dispersible solids.

EP-A 0,282,289 relates to a skin-care composition containing 1% to 35% by weight of a salt of a citric acid monoalkylester. A paraffin oil or vegetable oil is used as the carrier for this composition. This neither describes as prior art nor suggests using a hydrophilic moisture regulator as an additional component, especially one on the basis of polyols, specifically in conjunction with tissue products.

German Published Examined Application No. 2,622,571 relates to a moist toilet paper impregnated with cleansing, fatty and bacteriostatic substances, whereby the support material is impregnated with a solution having the following composition: 0.2% to 2.0% by weight of fatty acid amidoalkyl betaine, 0.2% to 2.0% by weight of ethoxylated glycerin partial ester of saturated fatty acids, 0% to 20% by weight of aliphatic alcohols having 2 to 4 carbon atoms, 0.5% to 5% by weight of organic acids, 0% to 0.5% by weight of perfume oil, and water as the rest. Due to the fraction of acids that are optionally to be added, a pH value of 5 to 6 is achieved. This publication likewise defines in detail what the aliphatic alcohol components are supposed to be, namely, disinfecting and preserving components, which normally means low alkyl monoalcohols, especially the representatives ethanol and isopropanol named in the publication. This neither describes as prior art nor suggests adding moisture regulators to this composition.

German Utility Model No. 8,512,083 discloses moist toilet paper which is characterized in that it consists of a paper impregnated with glycol or glycol ester. This document neither discloses nor does it suggest adding other components to the moist toilet paper which have a softness-enhancing effect as well as an emollient effect for the user.

AT 358,741 relates to a skin-cleansing web impregnated with cleansing emollient, in which the web has a wiping surface and a wiping zone of low density, whereby the wiping surface forms a boundary for the wiping zone, the wiping zone having a mean hollow space index of at least 68 and a minimum hollow space index of at least 10, and whereby the wiping zone is impregnated with 10% to 150% lipophilic cleansing emollient, relative to the weight of the web. However, the subject matter of the present invention is neither described as prior art nor suggested, since the composition according to the invention is not lipophilic vis-à-vis the hydrophilic main component, namely, the moisture regulator.

However, it is a virtually unknown objective to provide such a tissue product that has not only an improved softness but that additionally has an active skin-care effect thanks to the applied composition.

Thus, the subject matter of the invention is to provide a composition containing moisture regulators for tissue products that has a softness-enhancing effect as well as an emollient effect for the user.

SUMMARY OF THE INVENTION

Therefore, the present invention relates to a composition containing moisture regulators for tissue products which is characterized in that it also contains 1% to 25% by weight, preferably 7% to 20% by weight, especially 5% to 13% by weight, relative to the total composition, of at least one non-ionic surfactant selected from among amine oxide and/or hydroxy acid esters and/or at least one ampho-surfactant.

Another subject matter of the present invention is a process for the production of tissue products in which such a composition is applied onto the fiber web or onto the tissue sheet either within the wire section, the press section, the TAD section, on the Yankee cylinder and/or the drying section, that is to say, at a fibrous material density of 20% to 97% relative to the dry fiber weight of the sheet, in an amount of 0.1% to 59% by weight, continuously or discontinuously onto or into the sheet, and the sheet optionally undergoes a re-smoothing process after the application. As an alternative, the present invention is based on the objective of providing a process for the production of tissue products in which the above-mentioned application is carried out after the drying section on the lap machine, on the combiner and/or in the automatic processing unit in the above-mentioned manner.

Another aspect of the present invention is a process for the production of tissue products in which a composition is applied onto a fiber web or onto a tissue sheet within a wire section, a press section, a through-air drying section, on a Yankee cylinder and/or a drying section, at a fibrous material density of 20% to 97% relative to the dry fiber weight of the sheet, in an amount of 0.1% to 50% by weight, preferably 0.2% to 50% by weight, continuously or discontinuously onto or into the sheet, and wherein the sheet optionally undergoes a smoothing process after the application.

Another aspect of the present invention is a process for the production of tissue products, in which a composition is applied onto a fiber web or onto a tissue sheet after being treated by a drying section of a tissue paper machine, on a combiner and/or in a converting unit in an amount of 0.1% to 40% by weight, preferably 1% to 20% by weight, continuously or discontinuously onto or into the sheet, and the sheet optionally undergoes a smoothing process after the application.

Another subject matter of the present invention is a tissue product in the form of wet-laid, including TAD, and/or air-laid products or non-wovens on the basis of sheet-like support materials having at least one ply and containing primarily cellulose fibers, which is characterized in that it also contains 5% to 20% by weight, preferably 7% to 13% by weight, relative to the total product, of at least one special non-ionic surfactant, selected from among amine oxide and/or hydroxy acid esters and/or at least one ampho-surfactant.

Finally, the subject matter of the present invention is the use of the above-mentioned composition for the treatment of tissue products, especially facial tissues, cosmetic tissues, make-up removal wipes, toilet paper and household paper towels.

DETAILED DESCRIPTION OF PREFERRED EMBODIMENTS OF THE PRESENT INVENTION

According to a preferred embodiment of the composition according to the invention, the above-mentioned non-ionic surfactant is an amine oxide having the general formula

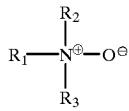
(I)

wherein $R_1$, $R_2$ and $R_3$, independent of each other, stand for an optionally substituted aliphatic, linear or branched alkyl radical having 1 to 25 carbon atoms, preferably 1 to 17 carbon atoms, for an optionally substituted, cyclic alkyl radical having 3 to 25 carbon atoms, preferably 3 to 17 carbon atoms, for an optionally substituted aliphatic, linear or branched amidoalkyl radical having 3 to 22 carbon atoms, preferably 7 to 17 carbon atoms in the alkyl part, or for an optionally substituted cyclic amidoalkyl radical having 3 to 10 carbon atoms, preferably 5 to 8 carbon atoms in the alkyl part.

With these amine oxides, it is preferable that, in the above-mentioned formula, $R_1$ and $R_2$ stand for an alkyl group having 1 to 4 carbon atoms, preferably methyl, and $R_3$ stands for an amidoalkyl group having the general formula $$(CH_2)_a N(H)C(O)R_4 \tag{II}$$

wherein a is 1 to 5 and $R_4$ stands for a fatty acid radical stemming from natural oils or fats and having 7 to 25 carbon atoms, preferably 7 to 17 carbon atoms.

According to another preferred embodiment, the compositions according to the invention contain a hydroxy acid ester, whereby it can be, for example, a glucose acid ester, a lactic acid ester, a mandelic acid ester, a malic acid ester, a tartaric acid ester, a citric acid ester or a ricinoleic acid ester, which contains at least one fatty acid radical stemming from natural oils or fats and having 1 to 25 carbon atoms, preferably 7 to 17 carbon atoms, and which optionally also has at least one polar group such as, for example, hydroxy. In this context, special preference is given to corresponding citric acid esters containing at least one fatty acid radical and to their salts.

According to another preferred embodiment, the composition according to the invention contains an amphosurfactant in the form of an ampholyte or a betaine.

If the component contained in the composition according to the invention is a betaine, then it should be derived from natural or synthetic sources and selected from among alkyl betaines having the general formula $$R_5(CH_3)N^{\oplus}(CH_3)CH_2COO^{\ominus} \tag{III}$$

wherein $R_5$ stands for an optionally substituted linear or branched alkyl group having 1 to 25 carbon atoms, preferably 7 to 17 carbon atoms, for alkylamido betaines having the general formula, $$R_6(CO)NH(CH_2)_o(CH_3)N^{\oplus}(CH_3)CH_2COO^{\ominus} \tag{IV}$$

wherein $R_6$ stands for an optionally substituted linear or branched alkyl group having 1 to 25 carbon atoms, preferably 7 to 17 carbon atoms, and o is 1 to 5, for sulfobetaines having the general formula

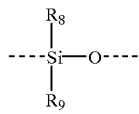
(VI)

wherein $R_7$ stands for an optionally substituted alkyl group having 1 to 25 carbon atoms, preferably 7 to 17 carbon atoms, and X stands for an optionally substituted alkylene group with 1 to 5 methylene units, for alkyl polyamphopolycarboxy glycinates having the general formula

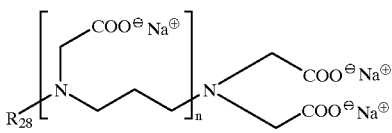
(XI)

wherein $R_{28}$, stands for a $C_7$ to $C_{17}$-fatty acid and n is 2 or 3 or glycine ester having the general formula

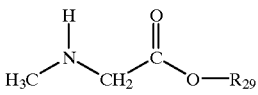
(XII)

wherein $R_{29}$ stands for a $C_7$ to $C_{17}$-Alkyl group, preferably $C_{12}H_{25}$.

In the composition according to the invention, it is also preferred for the moisture regulator to be present in an amount of 40% to 90% by weight, preferably 50% to 80% by weight, relative to the total composition, and for it to be selected especially from among polyols. Polyols as defined in the above-mentioned manner are especially glycerin, polyalkylene glycol, 1,3-butylene glycol (butylene glycol), propylene glycol and sugar alcohols, whereby especially glycerin, butylene glycol and/or propylene glycol are particularly preferred.

According to another preferred embodiment, the compositions according to the invention contain 0.01% to 50% by weight, preferably 0.1% to 40% by weight, of at least one natural, nature-identical or synthetic skin-care agent. Mention can be made here of skin-care agents on the, basis of vitamins or plant extracts such as, for example, extracts of horse chestnut seeds, birch, arnica, chamomile or bisabolol or else azulene itself, St. John's wort, cucumber, aloe vera, hops, allantoin or hamamelis and linden, some of which are also known for their astringent and healing effects. Provitamin B5=D-panthenol is especially well-suited since it concurrently serves as a moisturizer and thus partially replaces the glycerin/propylene glycol. In the case of bisabolol and azulene, an addition of 0.5% to 1% to the composition already brings about such an effect. Other ingredients that can be added to the composition are glycyrrhetinic acid, the active ingredient from the root of the licorice bush, which has a bacteriostatic and antiinflammatory effect and also its salts, as well as phytosterol (also ethoxylated) Generol® (Henkel KGaA), made of soy oil, which likewise has an antiinflammatory effect (R. Wachter, B. Salka and A. Magnet, Parfümerie and Kosmetik [Perfumery and Cosmetics] 75 (1994) 755). The composition can contain 1% to 5% by weight of these ingredients. Additional ingredients here are, for example, sorbitan fatty acid ester or oxethylated homologous compounds of glycerin, esters of oxethylated fatty alcohols, fatty alcohol alkanolamides, oxethylated fatty alcohols, oxethylated lanolin alcohols, glycerin monostearate, stearic acid, cetyl stearyl alcohol, vaseline and lanolin. In addition to lanolin itself, lanolin derivatives can also be used such as, for instance, lanolin alcohol or wool grease alcohols that are sold by Union Carbide Inc. under the name Amerchol, in conjunction with mineral oils. Other lanolin derivatives are the acetylated lanolins as well as hydrophilic lanolin derivatives, for example, lanolin polyoxyethylene compounds. The composition can also contain jojoba oil, avocado oil, tea shrub oil and linden extract or rice germ oil in an amount ranging from 1% to 40% by weight, but especially ranging from 10% to 20% by weight as additional beneficial skin-care components.

The polysiloxane component possibly used as an ingredient of the skin-care agent can be any water-soluble and/or water-dispersible compound that is liquid, pasty or wax-like at room temperature (20° C. [68° F.]). The polysiloxane component used for the purposes of the present invention includes polymeric, oligomeric, copolymeric and other multiple, monomeric siloxanes. Below, the term polysiloxane will refer to any polymeric, oligomeric, or other polymonomeric siloxane material. Moreover, the polysiloxane material can have a linear structure, a branched structure or a cyclic structure.

According to a preferred embodiment of the composition, the polysiloxane component in the skin-care agent has monomeric siloxane units having the following structure:

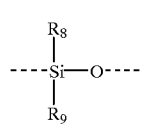

(VI)

wherein $R_8$ and $R_9$ are either the same or else different for each monomeric siloxane unit, and each stands for an alkyl, aryl, alkenyl, alkylaryl, arylalkyl, cycloalkyl, halogenated hydrocarbon or other group. Each of these groups can be substituted or unsubstituted. $R_8$ and $R_9$ groups of each special monomeric unit can differ from the corresponding functional groups of the next attached monomeric unit. Moreover, these groups can be straight-chained as well as branched or else they can have a cyclic structure. The groups $R_8$ and $R_9$ can also and independently of each other be silicon groups, but they are not limited to siloxanes, polysiloxanes and polysilanes. The groups $R_8$ and $R_9$ can also contain a large number of organic functional groups such as, for example, alcohol, carboxylic acid and amino-functional groups.

The degree and type of substitution determine the relative degree of softness, the velvety hand and the hydrophilia that is imparted to the tissue paper structure. In general, the degree of softness and the velvety hand—brought about, for example, by the polysiloxane—increase as the hydrophilia of the substituted polysiloxane component decreases. Amino-functional polysiloxanes and polyether polysiloxanes are especially preferred as the polysiloxane component in the treatment agent according to the invention.

Preferred skin-friendly polysiloxanes in the composition according to the invention include linear organopolysiloxane compounds having the following general formula

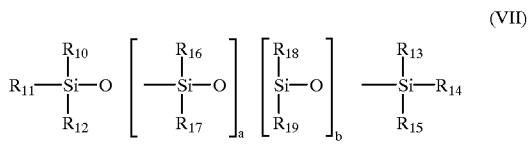

(VII)

wherein the $R_{10}$ to $R_{18}$ groups each, independently of each other, stand for $C_1$ to $C_{10}$ unsubstituted alkyl or aryl groups and $R_{19}$ stands for any substituted $C_1$ to $C_{10}$-alkyl or aryl radical. Preferably, each $R_{10}$ to $R_{18}$ group, independent of each other, stands for a $C_1$ to $C_{10}$ unsubstituted alkyl group. The person skilled in the art in this field knows that it does not make much difference, for example, whether $R_{18}$ or $R_{19}$ stands for the substituted group. Preferably, the molar ratio of b to (a+b) is between 0% and 20%, preferably between 1% and 10%, and especially between 1% and 5%.

In an especially preferred embodiment of the composition according to the invention, in the skin-friendly polysiloxane, $R_{10}$ to $R_{18}$ stands for methyl groups and $R_{19}$ stands for a substituted or unsubstituted alkyl, aryl or alkenyl group. The materials generally designated here as polydimethyl siloxanes are those which have a special functionality as they are used in the present case. Examples of such polydimethyl siloxanes can be polydimethyl siloxanes such as Dow Corning® 200 Fluid, polydimethyl cyclosiloxanes such as Dow Corning® 344 and 345, polydimethyl siloxane with an $R_{10}$-alkyl hydrocarbon group and a polydimethyl siloxane with one or more amino, carboxyl, hydroxyl, ether, polyether, aldehyde, ketone, amide, ester, thiol and/or other $R_{19}$ functional groups, including alkyl and alkenyl analogs of such functional groups. For example, an amino-functional alkyl group such as $R_{19}$ can be amino-functional polydimethyl siloxane or an amino-alkyl-functional polydimethyl siloxane. The polydimethyl siloxanes listed here are given as examples but this does not mean that others, not specifically mentioned here, are excluded from this.

The viscosity of the polysiloxanes used as the skin-friendly component in the composition according to the invention can vary over a wide range as long as the polysiloxane remains fluid and can be liquefied for use in the treatment agent according to the invention for application onto the tissue paper. This encompasses, for example, viscosities of $25\times10^{-6}$ m$^2$/s to $20,000,000\times10^{-6}$ m$^2$/s or even higher. Preference is given here to viscosities ranging from $15,000\times10^{-6}$ m$^2$/s to $3,400,000\times10^{-6}$ m$^2$/s. High-viscosity polysiloxanes, which are not themselves flowable, can be effectively applied onto tissue paper as a component of the composition according to the invention, for example, by emulsifying the polysiloxane component according to the invention in polyol or propylene glycol or glycerin or water or else dissolved in mixtures thereof together with a surfactant or else by dissolving the polysiloxane, if it is not soluble in propylene glycol or glycerin or water, using a solvent such as hexane. Special methods for applying the polysiloxane component onto tissue products are discussed below.

The above-mentioned skin-friendly polysiloxane components are described, for example, in U.S. Pat. Nos. 2,826,551, 3,964,550, 4,364,837, 4,395,454, 4,950,545, 4,921,895 and British Patent No. 849,433. Furthermore, the monograph "Silicon Compounds", pages 181 to 217 published by Petrarch Systems, 1984, contains a comprehensive listing and description of such polysiloxanes.

According to another preferred embodiment, polyether siloxanes having the general mean formula can be used as the skin-friendly polysiloxane component in the compositions according to the invention,

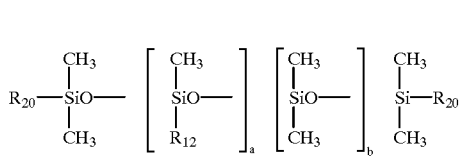
(VIII)

wherein $R_{20}$ in the molecule is either the same or else different and stands for an alkyl group having 1 to 12 carbon atoms or for a polyether group $(C_nH_{2n}O)_xR_{21}$, wherein $R_{21}$ stands for hydrogen, hydroxyl, alkyl or for an acyl group and n is a numerical value from 2 to 2.7, and x has a numerical value from 2 to 200, provided that at least one of the $R_{20}$ groups in the average molecule stands for a polyether group; a has a numerical value from 0 to 98, b has a numerical value from 0 to 98 and a+b is 8 to 98. $R_{20}$ can stand for an alkyl group having 1 to 12 carbon atoms or for a polyether group. However, the condition has to be met that at least one $R_{20}$ in an average molecule stands for a polyether group. Preferably, 2 to 5 of the $R_{20}$ groups stand for polyether groups and the remaining $R_{20}$ groups then stand for an alkyl group, whereby special preference is given to the methyl group. The alkyl group, however, can also have up to 12 carbon atoms. In this manner, it is possible to vary the properties of the treatment agent and thereby to improve the handling of tissue paper products. The polyether groups have the formula $(C_nH_{2n}O)_xR_{21}$. The index n has a numerical value from 2 to 2.7. In general, the ether group consists of several oxyethylenes and optionally oxypropylene groups. When the index n is 2, then the polyether group consists exclusively of oxyethylene units. If the numerical value of n increases, then the fraction of oxyethylene groups likewise increases. The numerical value of n=2.7 means that 70% of the polyether groups are oxypropylene groups.

The index x stands for the number of oxyalkylene units. This value is a mean numerical value since a mixture of products having different chain lengths is generally obtained from the synthesis of polyethers. The index x has a numerical value from 2 to 200 and preferably lies between 10 and 50. Preference is given to polyether groups with a mean molecular weight of 600 to 4000. The index a means the number of methyl siloxane units that are present on the $R_{12}$ group. The index b corresponds to the number of dimethyl siloxane units. Whereas a and b can assume a value from 0 to 98, the condition has to be met that the sum of a+b has a value from 8 to 98. If a=0, then the polyether group or groups are connected at their terminal positions. The siloxanes with positive values for a are modified by the $R_{12}$ side chains. Preference is given to siloxanes in which the $R_{20}$ groups are located in the side chain. The $R_2$ group can be hydrogen, hydroxyl, alkyl or else acyl. Preferably, $R_{13}$ stands for a hydrogen atom. If $R_{21}$, stands for an alkyl group, then low alkyl groups having 1 to 4 carbon atoms are preferred. The acetyl group is the preferred acyl group.

According to an especially preferred embodiment, the skin-friendly polysiloxane component in the composition according to the invention has the following formula:

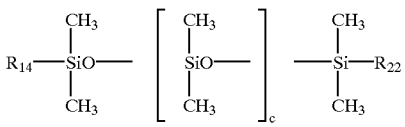
(IX)

wherein $R_{22}$ stands for a group having the formula

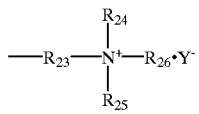
(X)

and wherein $R_{23}$ stands for a bivalent hydrocarbon group whose carbon chain is interrupted by an oxygen atom, $R_{24}$, $R_{25}$, $R_{26}$ are either the same or else different and stand for alkyl groups having 1 to 18 carbon atoms, of which one of the groups $R_{24}$, $R_{25}$, $R_{26}$ stands for a —$(CH_2)_3$ NHCOR$_{19}$ group wherein $R_{19}$ stands for an alkyl group having 7 to 17 carbon atoms and $Y^-$ is a monovalent anion and c has a numerical value from 50 to 100. $R_{23}$ stands for a bivalent hydrocarbon group, for example, for the group having the formula —$CH_2$—$C(OH)H$—$CH_2$—$O$—$(CH_2)_3$—. The $R_{24}$, $R_{25}$, $R_{26}$ groups can be either the same or else different and stand for alkyl groups having 1 to 18 carbon atoms. However, one of the above-mentioned groups $R_{24}$, $R_{25}$, $R_{26}$ can also stand for a $(CH_2)_3$ NHCOR$_{27}$ group.

If $R_{24}$, $R_{25}$, $R_{26}$ groups stand for alkyl groups, then they have 1 to 18 carbon atoms. Special preference is given to $R_{14}$ groups in which two of the above-mentioned $R_{24}$, $R_{25}$, $R_{26}$ groups have 1 to 4 carbon atoms and the third group has up to 18 carbon atoms. If one of the $R_{24}$, $R_{25}$, $R_{26}$ groups stands for a $(CH_2)_3$ NHCOR$_{27}$ group, then the $R_{19}$ group stands for an alkyl group having 7 to 17 carbon atoms. $Y^-$ is a monovalent anion, in general an acetate group. However, Y can also be an inorganic group such as, for example, Cl$^-$. The Index "c" indicates the number of dimethyl siloxy units in the linear siloxane and has a numerical value from 5 to 100 and preferably from 10 to 80. Among the above-mentioned siloxanes, special preference is given to polydimethyl siloxanes as such as well as, for instance, to polydimethyl siloxanes modified with polyether groups, with alkyl groups, and with quaternary or betainic groups, especially with nitrogen groups.

Especially preferred polysiloxanes are the organo-modified siloxanes sold by Th. Goldschmidt AG under the name Tegopren®, which have a pronounced surface activity and boundary surface activity in aqueous and organic systems. These are polyether siloxanes of the type offered for sale in the company publication "Tegopren® Informativ", undated, by Th. Goldschmidt AG under the trade names Tegopren® 3012, Tegopren® 3020, Tegopren® 3021, Tegopren® 3022, Tegopren® 3070, Tegopren® 5830, Tegopren® 5840, Tegopren® 5842, Tegopren® 5843, Tegopren® 5847, Tegopren® 5851, Tegopren® 5852, Tegopren® 5863, Tegopren® 5873, Tegopren® 5878, Tegopren® 5884 as well as Tegopren® 7006, and they normally have mean turbidity points in the range from below 25° C. [77° F.] to 71° C. [159.8° F.] as well as modified siloxanes in the form of Tegopren silicon quats and Tegopren silicon betaines of the type sold under the designations Tegopren® 6920, Tegopren® 6922 and Tegopren® 6950.

Non-ionic and/or cationic surfactants in quantities of 0% to 20% by weight, preferably 0% to 10% by weight, can be used in the composition according to the invention as additional commonly employed auxiliaries and additives. Such types of surfactants are, for example, quaternary ammonium compounds, especially quaternary ammonium salts such as those described, for example, in U.S. Pat. Nos. 5,312,522, 5,397,435, 5,405,501, 5,427,696 as well as in the patent applications EP-A 688,901, WO95/11344, WO95/11343, WO95/01478, WO95/01479, WO94/29521, WO94/29520, WO94/16143 and WO94/19381.

Moreover, the compositions according to the invention can contain commonly employed perfumes that have been selected from among natural, nature-identical or synthetic perfumes (see definition in Römpp, $9^{th}$ Edition, 1992, pp. 3887 f), whereby preference is given to the corresponding fragrances. Examples of such substances used here include citrus oils such as lemon oil, bergamot oil, orange oil, petit grain oil, pine oil, foin coupé perfume compositions or blossom oils such as, for example, rose, jasmine, lilac, lavender as well as synthetic fragrances on the basis of menthol, etc. An overview of this can be found in Ullmann, Enzyklopädie der technischen Chemie [Encyclopedia of Industrial Chemistry], Volume 20, pp. 190 to 285.

Furthermore, together with the composition according to the invention, it is also possible to add corresponding inorganic pigment or organic dyes of the type commonly employed in tissue and non-woven paper production. Here, not least of all for environmental reasons, preference is given to dyes that are physiologically safe and that do not irritate the skin, especially the corresponding natural or nature-identical dyes. All of the above-mentioned additives and auxiliaries can be present individually as well as in combination.

Moreover, the composition according to the invention can also contain inorganic and/or organic fillers of the type commonly used in the production of such products, for instance, talcum, bentonite and other types of clay.

The quantity of fillers added in this manner is usually 1% to 50% by weight, but preferably 1% to 10% by weight.

If so desired, the composition according to the invention can also contain gelling agents or hydrogels in the form of naturally occurring polymers, for example, on the basis of polysaccharides, lignin, caoutchouc, protein and/or natural resins. If polysaccharides are used here, then they are film-forming materials obtained from terrestrial plants, aquatic plants or microorganisms. Such gelling agents on the basis of polysaccharides from terrestrial plants are normally defined as starch and starch products, that is to say, for instance, corn, wheat and rice starch as well as potato starch and tapioca starch. Other polysaccharides extracted from terrestrial plants are galactoglucomannans, for example, St. John's bread seed meal and guar, dipectins and pectin substances, exudate gums such as gum Arabic or acacia gum as well as tragacanth, cellulose derivatives, etc. The polysaccharides obtained from aquatic plants are primarily alginates and agar, carragenans as well as algae polysaccharides. Last but not least, polysaccharides extracted from microorganisms are dextran and xanthan. Gelling agents on the basis of proteins that can be used in the compositions according to the invention are mainly gelatins which are usually commercially available as Type A and Type B. Synthetically modified, naturally occurring polymers that can be used in the compositions according to the invention as thickening components are the corresponding cellulose ethers, cellulose esters, starch esters and starch ethers as well as their mixtures. Finally, within the scope of the compositions according to the invention, it is also possible to use synthetic polymers that are selected from among polyvinyl compounds, preferably polyvinyl alcohol, polyvinyl pyrrolidone or polyvinyl butyral, from polyacrylic compounds, preferably polymethacrylic acid ester copolymers. These components can be added to the composition in amounts ranging from 0% to 40% by weight, preferably from 1% to 20% by weight.

An overview of such water-soluble polymers that can be used is found in the Encyclopedia of Polymer Science and Engineering, Volume 17 (1989), pp. 730 to 784.

The above-mentioned composition according to the invention normally has a pH value in the range from 3 to 8, but preferably from 3.5 to 5.

Normally, at the application temperatures ranging from 10° C. to 90° C. [50° F. to 194° F.], preferably from 15° C. to 80° C. [59° F. to 176° F.], the composition according to the invention has a viscosity of 1 to 700 mPas, preferably 5 mPas to 600 mPas when it is applied by spraying, and a viscosity of 5 to 2000 mPas, but preferably 10 mPas to 1500 mpas, when it is applied with a roller, doctor knife or blade.

In a preferred embodiment, the composition according to the invention contains the following components in the following amounts: 30% to 90% by weight, preferably 50% to 80% by weight of at least one moisture regulator, especially glycerin and/or propylene glycol, 0% to 20% by weight, preferably 2% to 10% by weight of at least one non-ionic and/or cationic surfactant, 1% to 25% by weight, preferably 2% to 20% by weight of at least one special non-ionic surfactant, selected from among amine oxide and/or hydroxy acid esters as well as at least one amphosurfactant, 0.01% to 40% by weight, preferably 0.01% to 20% by weight of at least one skin-care agent, 0% to 70% by weight, preferably 0% to 40% by weight of at least one natural, naturally modified or synthetic gelling agent, and water as the rest.

The subject matter of the present invention is also a process for the production of tissue products of the type described above, which is characterized in that a composition of the above-mentioned type is applied onto the fiber web or onto the tissue sheet either within the wire section, the press section, the TAD section, on the Yankee cylinder and/or the drying section, that is to say, at a fibrous material density of 20% to 97% relative to the dry fiber weight of the sheet, in an amount of 0.1% to 40%, preferably 1% to 20%, continuously or discontinuously onto or into the sheet, and the sheet optionally undergoes a re-smoothing process.

In an alternative embodiment, the present invention relates to a process for the production of tissue products, which is characterized in that a composition of the above-mentioned type is applied onto the fiber web or onto the tissue sheet after the drying section on the lap machine, on the combiner and/or in the automatic processing unit in an amount of 0.1% to 40% by weight, preferably 1% to 20% by weight, continuously or discontinuously onto or into the sheet, and the sheet optionally undergoes a re-smoothing process after the application.

In preferred embodiment of the process according to the invention, the composition, at a fibrous material density of 35% to 97% relative to the dry fiber weight of the single-ply sheet, is applied in an amount of 0.2% to 50%, but preferably 1% to 20%.

According to another preferred embodiment of the process according to the invention, the tissue sheet is a multi-ply sheet and the composition, at a fibrous material density of more than 90% relative to the dry fiber weight, is applied onto or into at least one of the outer plies of the multi-ply sheet in an amount of 0.001% to 50%, detected as an individual component, e.g. by means of headspace gas chromatography, preferably 0.01% to 30%, or more preferred 0.1% to 25%, especially preferred 0.5% to 20%.

According to another preferred embodiment of the process according to the invention, the composition is applied onto and/or in the multi-ply tissue sheet on both outer plies in an amount of 0.001% to 50%, preferably 0.01% to 30%.

In another preferred embodiment of the process according to the invention, the composition is applied in the tissue production machine by means of spray application onto the Pope roller while generating a treatment agent film and by its subsequent transfer onto the tissue sheet, which is done either during the rolling procedure or else the application is done by means of a doctor knife or blade process. The application can also be done by means of rollers, spray devices, the doctor knife or blade process.

As an alternative, the composition, especially the skin-care agent, can be applied into the tissue sheet in micro-encapsulated form, embedded in micro-sponges or in the form of liposomes.

In another preferred embodiment of the process according to the invention, in cases where the application is not done in micro-encapsulated form, embedded in micro-sponges or in the form of liposomes on or in the plies, a re-smoothing process is carried out by passing the tissue sheet through the gap of a pair of rollers in which one roller with a steel surface is paired with a mating roller having a steel, plastic, paper or rubber surface, preferably a plastic surface. Within the scope of this process modification, it is advantageous to carry out the re-smoothing process by feeding the tissue sheet or the non-woven twice through a gap of a pair of rollers, in which first a roller having a steel surface is paired with a mating roller having a plastic surface and then, in mirror image, a roller having a plastic surface is paired with a roller having a steel surface.

According to another preferred embodiment of the process according to the invention, the above-mentioned composition is applied onto the fiber web or non-woven within the scope of conventional fiber production or a non-woven web-laying process. As an alternative, the composition can also be applied onto the fiber web within the scope of a through-air drying or TAD process.

Another subject matter of the present invention is the use of the above-mentioned composition for the treatment of tissue products, especially facial tissues, cosmetic tissues, make-up removal wipes, toilet paper and household paper towels.

Another subject matter of the present invention is a tissue product in the form of wet-laid, including TAD, and/or air-laid products or non-wovens on the basis of sheet-like support materials having at least one ply and containing primarily cellulose fibers, which is characterized in that it also contains 0.05% to 50% by weight, preferably 1% to 30% by weight, relative to the total product, of at least one special non-ionic surfactant, selected from among amine oxide and/or hydroxy acid esters and/or at least one ampho-surfactant.

The above-mentioned tissue product according to the invention can be an at least single-ply, preferably two-ply to four-ply or multi-ply tissue paper that is unembossed, embossed or partially embossed, for example, a tissue paper provided with decorative embossing along the edge. Instead of pure cellulose fibers, it is also possible to use tissue papers with unembossed middle plies as well as a middle ply made of CTMP. If a multi-ply tissue paper is used, the requisite ply adhesion can be achieved by full-surface gluing, by partial gluing, for example, by applying dots of adhesive to match a given pattern, by compressing the plies together with a steel—steel roller under pressure, through a mechanical adhesion of the individual plies over the surfaces, by means of a grid pattern, by means of edge embossing, by means of knurling, etc. Such a tissue product can be a bulky support material with sufficient strength and the greatest possible softness, which can be achieved, for example, using tissue, non-woven or a combination of both materials. When tissue is used here, products with a basis weight of about 15 to 75 g/m$^2$ are selected, whereas a basis weight of 18 to 120 g/m$^2$ is selected when non-woven products are used. This process can be used for either tissue products and non-woven products alone or else in a combination of both of them, each with different basis weights. The compressibility can be ensured through the use of non-wovens.

If so desired, such support material can also be imparted with wet-strength, whereby conventional wet-strength agents, which are not hazardous to health, for example, urea and melamine resins as well as cross-linked cationic poly-alkylene amines, etc. are used.

In a preferred embodiment, the tissue product according to the invention has a composition of the above-mentioned type on at least part of its surface, on its outer sides, on the insides of the outer plies, only on the inner plies or on all of the plies.

According to another preferred embodiment of the tissue product according to the invention, at least part of the above-mentioned composition is found on or in the plies as an application in micro-encapsulated form, embedded in micro-sponges or in the form of liposomes, and preferably at least part of the skin-care agent of the above-mentioned type is found on or in the plies in micro-encapsulated form, embedded in micro-sponges or in the form of liposomes.

As its basic component, in addition to the surfactant according to the invention, the above-mentioned composition contains the moisture regulators, and water as the rest. Polyols such as, for example, polyethylene glycol or sorbite or other skin-compatible and mucous membrane-compatible substances function as such moisture regulators. Here preference is given to the use of propylene glycol and/or glycerin.

As far as the skin-care agents are concerned, special preference is given to provitamin B5, the so-called D-panthenol, because of its very good moisture-retention properties. Other especially preferred skin-care components are allantoin and the addition compound of allantoin to D-panthenol, tocopherol acetate, jojoba oil, rice germ oil, avocado oil, special lactic acid-fatty alcohol ester, for example, the product made by Merck AG, namely, Ceraphyl® 28 H(CH$_3$)C(OH)C(O)OC$_{16}$H$_{33}$, phytosterol, glycyrrhetinic acid, and their salts, isopropylester of wool grease fatty acids made by the Nordmann & Rassmann company, for example, the isopropyl myristate sold under the brand name Amerlate® P, bisabolol and azulene, plant proteins such as, for example, wheat proteins and algae extracts as well as various plant extracts or active ingredients from hops, St. John's wort, balm, arnica, althaea, elderberry, sage, mallow, hamamelis, mango, papaya and linden.

As representatives of the amine oxides according to the invention, of hydroxy acid esters and of ampho-surfactants of especially preferred substance classes, the compositions according to the invention contain amine oxides having the formula

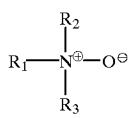

(I)

wherein $R_1$ and $R_2$ stand for methyl and $R_3$ stands for an amidoalkyl group having the general formula $(CH_2)_3N(H)C(O)R_4$, wherein $R_4$ stands for a $C_7$ to $C_{17}$ fatty acid radical. Especially preferred ampho-surfactants are so-called alkylamphoacetates having the general formula $R_8(O)C(H)N(CH_2)_2(H)NCH_2(OH)CCH_2COO^-$, wherein $R_8$ stands for a fatty acid radical having 7 to 17 carbon atoms. Moreover, alkyl polyamphopolycarboxy glycinates (APAC) are particularly preferred in which, in turn,

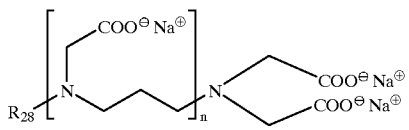

wherein $R_{28}=C_7$ to $C_{17}$ fatty acid, and n=2.3.

Furthermore, mention should be made here of trimethyl glycine having the general formula $(CH_3)_3N^+CH_2COO^-$, a cocoamidopropyl betaine or a citric acid monoglyceride with a $C_7$ to $C_{17}$ fatty acid radical, in which one of the two free citric acid carboxyl groups in the β-position has an $SO_3$ group.

Moreover, mention should be made of glycine esters having the general structure

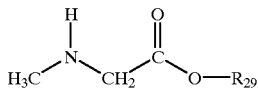

wherein $R_{29}=C_7$ to $C_{17}\rightarrow$—$C_{12}H_{25}$ (specifically: Medialan® LD, Example 5).

When the above-mentioned composition is used, it penetrates partially into the tissue fiber web, thereby influencing the softness and feel of the cloth. When the composition is applied exclusively onto the outer ply, enough lotion remains adhering to the top ply to be transferred onto the skin where it can develop its effect when the lotion-treated cloth is properly used.

In order to evaluate the improved/changed feel in comparison to standards, so-called hand-feel tests were carried out. This is done in the form of a panel test by trained persons, similar to the Manual of Sensory Testing Methods, (ISTN, Special Technical Publication 434, page 22, test form de-ranking methods, rank order eleventh printing, February 1993). On this basis, the increasing softness, defined here as the sum of the surface softness and crumple softness, is evaluated by a group of four trained persons by means of the following method:

The paper facial tissues to be tested were folded twice in half so that the sample identification could not be seen by the test person and in each case, the same outer side was presented for evaluation.

The tissues folded in this manner are then tested by being rubbed and crumpled between the test person's thumb, ball of the thumb and finger and then compared to previously defined standards. Whereas the "zero sample", i.e. an untreated facial tissue from the standard production, has a hand-feel value of just 72 hand-feel points on a scale from 0 to 100, the tissues that were lotion-treated in the laboratory are consistently ranked higher. The table below gives an overview of the increase in softness.

The present invention will now be explained with reference to embodiments.

EXAMPLE 1

10% by weight of citric acid alkyl polyglycol ester sulfosuccinate and disodium salt (Rewopol SB CS 50 made by REWO GmbH) are added to a basic lotion of 40% by weight of glycerin, 30% by weight of propylene glycol and 20% by weight of water. The addition is made while stirring, and thorough mixing has to be insured. A clear composition results in the form of a lotion that is applied onto a four-ply, edge-embossed tissue paper with a basis weight of 60 g/m² at a 6%-application. After being conditioned for 24 hours, the tissues are re-smoothed and lined up with other samples in a panel test. The lotion-treated tissue was always classified as softer than the sample without lotion; this was true of the samples that had been re-smoothed as well as those that had not been re-smoothed.

EXAMPLE 2

10% by weight of a cocoamidoalkyl dimethyl amine oxide of the type sold by the Th. Goldschmidt AG company under the designation Tegotain WS 35 is added to a basic lotion of 40% by weight of glycerin, 30% by weight of propylene glycol and 20% by weight of water. The addition is made while stirring, and thorough mixing has to be insured. A clear lotion results which is applied in a 6%-application onto a four-ply, edge-embossed tissue paper as described in Example 1. After a 24-hour conditioning phase, the tissues are re-smoothed and lined up with other samples in a panel test. In each case, the lotion-treated tissue yielded better results than a cloth without lotion, irrespective of whether they had been re-smoothed or not re-smoothed.

EXAMPLE 3

10% by weight-of the amine oxide as described in Example 2 was added to a basic lotion of 50% by weight of propylene glycol and 20% by weight of water and mixed thoroughly while being stirred. Subsequently, 20% by weight of D-panthenol (BASF AG) is added. The addition is carried out with vigorous stirring so that a thorough mixing is ensured. After a homogeneous lotion has formed, it is applied in a 6%-application onto a four-ply, edge-embossed tissue paper as described in Example 1. After being conditioned for 24 hours, the cloth is re-smoothed and likewise tested in a panel test. The lotion-treated tissue paper was once again classified as better than a tissue without lotion (re-smoothed or not re-smoothed),

EXAMPLE 4

5.25% by weight of amine oxide as described in Example 2 is added to a basic lotion of 30% by weight of glycerin and 20% by weight of propylene glycol and 29.75% by weight of water. Subsequently, another 15% by weight of Phytosterol (Henkel KGAA) is added. After thorough mixing, the lotion is applied in a 6%-application onto a four-ply, edge-embossed tissue paper as described in Example 1. After being conditioned for 24 hours and re-smoothed, the lotion-treated cloth was always classified in a panel test as better than a cloth that was not treated with lotion.

EXAMPLE 5

As the surfactant, 2% by weight of the amine oxide as described in Example 2 as well as 2% of Medialan® LD and, as the skin-care agent, 3% by weight of tocopherol acetate, 12% by weight of rice germ oil and 15% by weight of jojoba oil are added to a basic lotion of 46% by weight of propylene glycol and 20% by weight of water. After being thoroughly mixed, the lotion is applied in a 6%-application onto a four-ply, edge-embossed tissue paper as described in Example 1. After being conditioned for 24 hours and re-smoothed, the lotion-treated cloth was always classified in a panel test as better than a cloth that was not treated with lotion.

EXAMPLE 6

Example 2 was repeated, but instead of the amine oxide, 10% by weight of the alkylamphoacetate Rewoteric AM 2C NM (Witco Surfactants company),

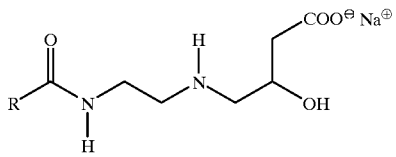

R=$C_7$ to $C_{17}$ fatty acid was added. After the application and the conditioning as well as re-smoothing, but otherwise with the same technique, it was found in a panel test that the lotion-treated tissue yielded better results than the corresponding tissue without lotion in every case.

EXAMPLE 7

10% by weight of the amine oxide as described in Example 2 was added to a basic lotion of 69% by weight of propylene glycol and 20% by weight of water as described in Example 2 and mixed well while being stirred. Subsequently, while the mixture is being heated to about 60° C. [140° F.] and vigorously stirred, 1% by weight of glycyrrhetinic acid (Midas Pharma GmbH, Ingelheim, Germany) is added. After dissolution and subsequent cooling off to 20° C. [68° F.], the lotion was applied in a 6%-application onto a four-ply, edge-embossed tissue paper as described in Example 1. After being conditioned for 24 hours and re-smoothed, the lotion-treated cloth was classified in a panel test as better than a cloth that was not treated with lotion.

EXAMPLE 8

Example 2 was repeated except that, instead of the amine oxide, 10% trimethyl glycine (WITCO company) was added. With an otherwise identical process methodology, a clear lotion was obtained which was applied in a 6%-application onto a four-ply, edge-embossed tissue paper as described in Example 1. After being conditioned for 24 hours and re-smoothed, the lotion-treated cloth was classified in a panel test as better than a cloth that was not treated with lotion.

EXAMPLE 9

4% of a bentonite (Optigel® SH, Süd-Chemie AG) was added to a basic lotion consisting of propylene glycol, glycerin and water (quantity ratio 30:45:25). The viscosity of the basic lotion thus treated was increased to about 840 mPas in order to allow an application by means of film-pressing. This lotion was applied on both sides in a 6%-application, yielding a hand-feel value of 77 with a fluctuation range of ±5.

| Lotion No. | Lotion | HF value |
|---|---|---|
| N | zero sample, not lotion-treated | 72 |
| S | glycerin + PG + water = 45 + 30 + 25 | 76 |
| Example 1 | Rewopol SB CRASTIN 50 + glycerin + PG + water = 10 + 40 + 30 + 20 | 76 |
| Example 2 | amine oxide WS 35 + glycerin + PG + water = 10 + 40 + 30 + 20 | 77 |
| Example 3 | D-panthenol + amine oxide WS 35 + PG* water = 20 + 10 + 50 + 20 | 75 |
| Example 4 | glycerin + PG + $H_2O$ + WS 35 + phytostyrene = Generol® 122 E 25 (Henkel) = 30 + 20 + 29, 75 + 5, 25 + 15 | 78 |
| Example 5 | PG + $H_2O$ + WS 35 + Medialan ® LD + tocopherol acetate + rice germ oil + jojoba oil = 46 + 20 + 2 + 2 + 3 + 12 + 15 | 76 |
| Example 6 | Rewoteric AM 2C** NM + glycerin + PG + water = 10 + 40 + 30 + 20 | 76 |
| Example 7 | Glycyrrhetinic acid + amine oxide WS 35 + PG + water =1 + 10 + 69 + 20 | 75 |
| Example 8 | Trimethyl glycine + glycerin + PG + water = 10 + 40 + 30 + 20 | 76 |
| Example 9 | glycerin + PG + $H_2O$ + bentonite = 45 + 30 + 25 + 4 | 77 |

HF = hand-feel
PG = propylene glycol
*Dodecyl-dimethyl amine oxide (Th. Goldschmidt AG)

What is claimed is:

1. A tissue product in a form of a wet-laid or air-laid product or a non-woven product of a sheet support material having at least one ply and containing primarily cellulose fibers, comprising a composition containing a moisture regulator in an amount of 40% to 90% by weight, and at least one non-ionic surfactant in an amount of 1% to 25% by weight of the composition, wherein the surfactant comprises an amine oxide and/or hydroxy acid esters and/or at least one ampho-surfactant, except for myristyl acetate and sodium salts of fatty alcohol acetates, wherein the composition is present on at least part of its surface, on its outer sides, on the insides of the outer plies, only on the inner plies or on all of the plies.

2. The tissue product according to claim 1, wherein the amount of the non-ionic surfactant is 5% to 20% by weight of the composition.

3. A tissue product in a form of a wet-laid or air-laid product or a non-woven product of a sheet support material having at least one ply and containing primarily cellulose fibers, comprising a composition containing a moisture regulator in an amount of 40% to 90% by weight, and at least one non-ionic surfactant in an amount of 1% to 25% by weight of the composition, wherein the surfactant comprises an amine oxide and/or hydroxy acid esters and/or at least one ampho-surfactant, except for myristyl acetate and sodium salts of fatty alcohol acetates, wherein at least part of the composition is present as an application, in micro-encapsulated form, embedded in micro-sponges or in the form of liposomes on or in the plies.

4. The tissue product according to claim 3, wherein at least one natural, nature-identical or synthetic skin care agent is present in micro-encapsulated form, embedded in micro-sponges or in the form of liposomes on or in the plies.

5. The tissue product according to claim 3, wherein the amount of the non-ionic surfactant is 5% to 20% by weight of the composition.

6. A process for production of tissue products, comprising applying a composition containing a moisture regulator for tissue products onto a fiber web or onto a tissue sheet within a wire section, a press section, a through-air drying section, on a Yankee cylinder and/or a drying section, at a fibrous material density of 20% to 97% of a dry fiber weight of the sheet, wherein the application is carried out in an amount of 0.001% to 50% by weight, continuously or discontinuously onto or into the web or sheet, and wherein the web or sheet optionally undergoes a smoothing process after the application, said composition comprising at least one non-ionic surfactant in an amount of 1% to 25% by weight of the composition, wherein the surfactant comprises at least one amine oxide and/or hydroxy acid esters, except for myristyl acetate and sodium salts of fatty alcohol acetates, and/or at least one ampho-surfactant, and wherein the moisture regulator is present in an amount of 40% to 90% by weight of the total composition.

7. The process according to claim 6, wherein the tissue sheet is a multi-ply sheet and the composition, at a fibrous material density of more than 90% of the dry fiber weight, is applied onto the multi-ply sheet, in an amount of 0.1% to 50% by weight.

8. The process according to claim 7, wherein the composition is applied onto at least one of outer plies of the multi-ply sheet in an amount of 0.1% to 50%.

9. The process according to claim 6, wherein at least part of the composition is applied onto the sheet by spraying, rolling or by means of a (roll) doctor knife or blade process, or into and/or onto the sheet in micro-encapsulated form, embedded in micro-sponges or in the form of liposomes.

10. The process according to claim 6, wherein the smoothing process comprises passing the tissue sheet or a non-woven sheet at least once through a gap of a pair of rollers in which one roller with a steel surface is paired with a mating roller having a steel, plastic, paper or rubber surface.

11. The process according to claim 10, wherein the mating roller has a plastic surface.

12. The process according to claim 6, wherein the smoothing process comprises feeding the tissue sheet or a non-woven sheet twice through a gap of a pair of rollers, in which first a roller having a steel surface is paired with a mating roller having a plastic surface and then, in mirror image, a roller having a plastic surface is paired with a roller having a steel surface.

13. The process according to claim 6, wherein the composition is applied onto the fiber web.

14. The process according to claim 6, wherein the composition is applied onto the fiber web by a through-air drying process or by a non-woven web-laying process.

15. The process according to claim 6, wherein the composition is applied in an amount of 0.2% to 50% by weight.

16. The process according to claim 6, wherein the tissue sheet is a multi-ply tissue sheet, and wherein the composition is applied onto the multi-ply tissue sheet, in an amount of 0.01% to 30% by weight.

17. The process according to claim 6, wherein the tissue sheet is a multi-ply tissue sheet, and wherein the composition is applied onto at least one of the outer plies of the multi-ply tissue sheet in an amount of 0.01% to 30% by weight.

18. A process for production of tissue products, comprising applying a composition containing a moisture regulator for tissue products onto a fiber web or onto a tissue sheet after being treated by a drying section of a tissue paper machine, on a combiner and/or in a converting unit, wherein the application is carried out in an amount of 0.1% to 50% by weight, continuously or discontinuously onto or into the web or sheet, and the web or sheet optionally undergoes a smoothing process after the application, said composition comprising at least one non-ionic surfactant in an amount of 1% to 25% by weight of the composition, wherein the surfactant comprises at least one amine oxide and/or hydroxy acid esters, except for myristyl acetate and sodium salts of fatty alcohol acetates, and/or at lest one ampho-surfactant, and wherein the moisture regulator is present in an amount of 40% to 90% by weight of the total composition.

19. The process according to claim 18, wherein the composition, at a fibrous material density of 35% to 97% of the dry fiber weight of a single ply of the tissue sheet, is applied in an amount of 0.2% to 40%.

20. The process according to claim 19, wherein the composition is applied in an amount of 1% to 20% by weight.

21. The process according to claim 18, wherein the composition is applied in an amount of 1% to 20% by weight.

22. A process for production of a multi-ply tissue product, comprising applying a composition containing a moisture regulator for tissue products onto a multi-ply tissue sheet within a wire section, a press section, a through-air drying section, on a Yankee cylinder and/or a drying section, at a fibrous material density of 20% to 97% of a dry fiber weight of the sheet, wherein the application is carried out in an amount of 0.001% to 50% by weight, continuously or discontinuously onto or into the web or sheet, and wherein the web or sheet optionally undergoes a smoothing process after the application, said composition comprising at least one non-ionic surfactant in an amount of 1% to 25% by weight of the composition, wherein the surfactant comprises at least one amine oxide and/or hydroxy acid esters, except for myristyl acetate and sodium salts of fatty alcohol acetates, and/or at least one ampho-surfactant, and wherein the moisture regulator is present in an amount of 40% to 90% by weight of the total composition.

23. The process according to claim 22, wherein the composition is applied onto at least one of outer plies of the multi-ply tissue sheet in an amount of 0.1% to 50%.

* * * * *